(12) United States Patent
Kawamura (10) Patent No.: US 6,779,526 B2
(45) Date of Patent: Aug. 24, 2004

(54) APNEA PREVENTION GEAR

(76) Inventor: Yasuo Kawamura, 3-98, Ozaki-kita-machi, Kakamigahara-shi, Gifu-ken 504-0002 (JP)

( * ) Notice: Subject to any disclaimer, the term of this patent is extended or adjusted under 35 U.S.C. 154(b) by 19 days.

(21) Appl. No.: 10/219,969

(22) Filed: Aug. 15, 2002

(65) Prior Publication Data

US 2004/0031492 A1 Feb. 19, 2004

(51) Int. Cl.[7] .................................................. A61F 5/56
(52) U.S. Cl. ...................... 128/848; 602/902; 128/874
(58) Field of Search .............................. 128/846, 848, 128/874, 875; 602/902, 19

(56) References Cited

U.S. PATENT DOCUMENTS

| | | | | |
|---|---|---|---|---|
| 2,632,178 | A | * | 3/1953 | Kennedy .................. 128/78 |
| 4,120,297 | A | * | 10/1978 | Rabischong ......... 128/DIG. 20 |
| 4,274,673 | A | | 6/1981 | Kifferstein |
| 4,682,588 | A | | 7/1987 | Curlee |
| 5,016,303 | A | | 5/1991 | Tanaka et al. |
| 5,738,640 | A | | 4/1998 | Carlson-Orsi |
| 5,920,932 | A | | 7/1999 | Hershgordon |
| 2001/0015208 | A1 | | 8/2001 | Konishi |

FOREIGN PATENT DOCUMENTS

| | | |
|---|---|---|
| EP | 396962 | 8/1933 |
| EP | 0363327 | 4/1990 |
| EP | 0 461 319 A1 | 11/1990 |
| EP | 671 A1 | 9/1999 |
| JP | 3009844 | 4/1995 |
| JP | 3069343 | 5/2000 |
| JP | 2000287803 | 10/2000 |
| KR | 1999-37189 | 10/1999 |
| KR | 2001-2277 | 1/2001 |

* cited by examiner

Primary Examiner—Michael A. Brown
(74) Attorney, Agent, or Firm—Robert D. Buyan; Stout, Uxa, Buyan & Mullins, LLP (57) ABSTRACT

There is provided a gear for preventing a user from lapsing into an apneic state by maintaining the body of said user in an inclined posture during said user's sleep. The gear includes a clothing body worn by said user and a pad. The clothing body includes a back body and a front body. The pad is attached to the back body of the clothing body and extends in the longitudinal direction. The pad includes a plurality of segments arranged along the longitudinal direction, capacities of the segments are different from each other, and each segment is expanded in accordance with the capacity thereof by a fluid to be supplied to each segment.

12 Claims, 6 Drawing Sheets

APNEA PREVENTION GEAR

BACKGROUND OF THE INVENTION

The present invention relates to a gear for reducing adverse effects by sleep apnea syndrome. More particularly, the present invention relates to a gear which can prevent a patient from lapsing into an apneic state when the soft palate or the like closes the upper airway by maintaining the head of the patient in an inclined state while asleep.

Sleep apnea syndrome is a disorder having a symptom in which breathing stops for 10 seconds or more during sleep due to various causes. Many cases of the sleep apnea syndrome can be satisfactorily remedied by improving living habits. The apnea syndrome is provoked when the nose wings, the soft palate, the pendulous palate, the tongue root, the pharyngeal palate or the like closes the upper airway during sleep, and obstruction especially by the soft palate has often been reported. Obstruction of the upper airway during sleep is dissolved when each of the above-described organs is arranged at a position where it does not close the upper airway.

The easiest cure of the upper airway obstruction is to arrange the head at an optimum position while asleep. Furthermore, the habitual stertor which is often observed among middle-aged and elderly males is considered as an obstructive sleep apnea syndrome-to-be, and preventing the habitual stertor generally leads to suppression of occurrence of this disease.

Conventionally, as this type of gear, there has been known a pillow for recumbency disclosed in Japanese Registered Utility Model No. 3009844. This pillow for recumbency allows mainly a patient of the sleep apnea syndrome to sleep in a recumbent position so that obstruction of the rhinopharyngeal part due to downward displacement of the tongue root or the like can be avoided.

In this pillow for recumbency, a tabular plate is provided at the bottom of a pillow pouch, and three cores (a first core, a second core and a third core) having different shapes are arranged on the plate. The first, second and third core are formed in the substantially elliptic, cylindrical shapes by filling a core material in the pouch in such a manner that these cores have different heights.

According to this utility model, a comfortable sleep can be obtained while maintaining the recumbent posture without effort by placing the head on this pillow for recumbency during sleep. Maintaining this recumbent posture prevents the rhinopharyngeal part from being obstructed even if the tongue root is displaced downward, thereby preventing lapsing into the apneic state.

However, in the prior art pillow for recumbency, each core is formed of a material having the hardness which rarely loses shape, and the height of each core is formed so as to be fixed to a predetermined height. Therefore, the hardness or height cannot be freely adjusted in accordance with preferences of each user. Thus, when the hardness or height of the pillow for recumbency is unsuitable, it is very difficult to sleep while holding the recumbent posture as mentioned above, and lapsing into the apneic state cannot be sufficiently prevented.

The present invention is based on the above-described problems existing in the prior art. It is the objective of the present invention to provide a gear which can readily reduce the apneic states during sleep.

SUMMARY OF THE INVENTION

To achieve this objective, according to the present invention, there is provided a gear for preventing a user from lapsing into an apneic state by maintaining the body of the user in an inclined posture during sleep. This gear includes a clothing body worn by a user and a pad. The clothing body includes a back body and a front body. The pad is attached to the back body of the clothing body and extends in the longitudinal direction. This pad includes a plurality of segments arranged along the longitudinal direction. Capacities of the segments are different from each other, and each segment expands in accordance with its capacity by a fluid supplied to each segment.

Therefore, a user wearing the gear can maintain his or her body inclined for a long period of time during sleep, thereby preventing the user from lapsing into an apneic state while asleep.

BRIEF DESCRIPTION OF THE DRAWINGS

FIG. 2($a$) is a front view showing a pad used in the vest illustrated in FIG. 1, and FIG. 2($b$) is a cross-sectional view of the pad taken along line 2$b$–2$b$ in FIG. 2($a$);

DETAILED DESCRIPTION OF THE PREFERRED EMBODIMENT

A preferred embodiment of a gear for preventing an apneic state according to the present invention will now be described in detail hereinafter with reference to the accompanying drawings.

Figure 1:
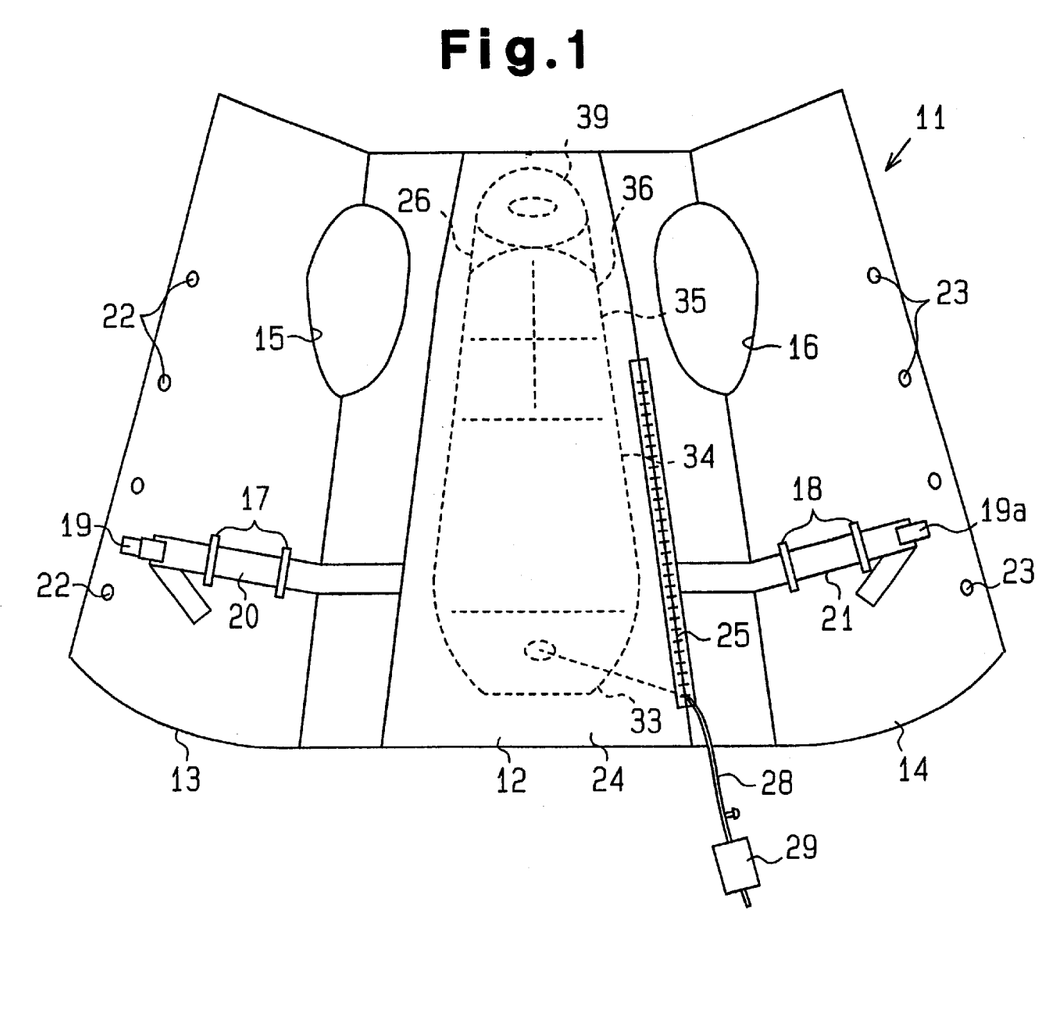
FIG. 1 is a front view showing a developed state of a vest according to an embodiment of the present invention.

As shown in FIG. 1, a clothing body constituting the gear for preventing the apneic state, namely, a vest 11 is formed of a cotton cloth and includes a back body 12, a right front body 13 and a left front body 14. A right hole 15 and a left hole 16 into which a user put the right and left arms are respectively formed between the back body 12 and the right front body 13 and between the back body 12 and the left front body 14.

A plurality of belt loops 17 and 18 are attached on the inner surfaces of the right front body 13 and the left front body 14. A right belt piece 20 including a tongue 19 is inserted into the belt loops 17 of the right front body 13, and the base end of the right belt piece 20 is fixed to the back body 12. A left belt piece 21 including a buckle 19a is inserted into the belt loops 18 of the left front body 14, and the base end of the left belt piece 21 is fixed to the back body 12. The tongue 19 and the buckle 19a are attached to the corresponding belt pieces 20 and 21 so as to be capable of adjusting positions. The tongue 19 is detachably engaged with the buckle 19a. When the user is wearing the vest 11, the right and left belt pieces 20 and 21 fix the vest 11 to the body of the user by inserting the tongue 19 into the buckle 19a by the user in front of the belly as shown in FIG. 2.

A plurality of convex clamps 22 and a plurality of concave clamps 23 which can be engaged with each other are respectively attached to the edges of the right front body 13 and the left front body 14 so that the right front body 13 is fixed to the left front body 14 by fixing these clamps 22 and 23 to each other when wearing the vest 11.

Figure 2A:
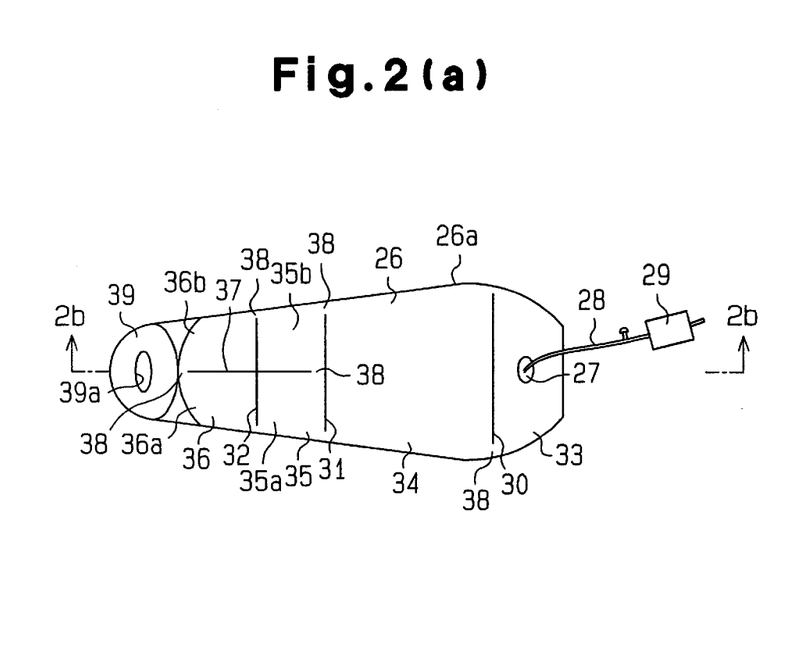
Figure 2B:
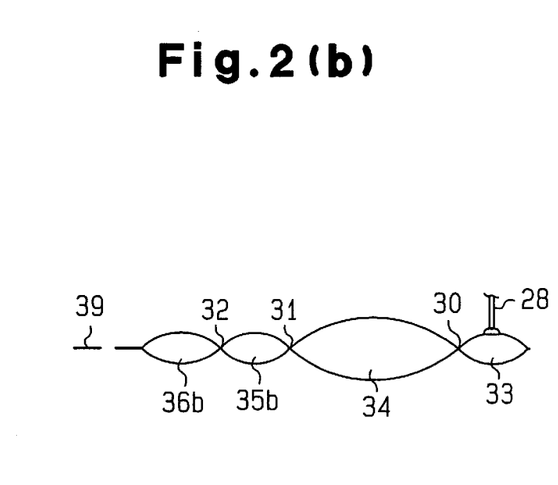

A bag-like accommodation portion 24 is formed on the inner surface of the back body 12, and a fastener 25 used for opening or closing an opening of the accommodation portion 24 is attached to the accommodation portion 24. A back pad 26 shown in FIGS. 2(a) and 2(b) is removably accommodated in the accommodation portion 24. The back pad 26 is formed into a bag-like hollow shape by welding peripheral edges 26a of two synthetic resin films, and a pump 29 is connected through a tube 28 to an air inlet 27 of the back pad 26. Operating the pump 29 enables filling of air into the back pad 26, adjustment of an air pressure in the back pad 26, and removal of the air from the inside of the back pad 26.

The inside of the back pad 26 is partitioned into four segments, i.e., first, second, third and fourth segments 33, 34, 35 and 36 by first, second, and third partitions 30, 31 and 32 extending in the widthwise direction of the back pad 26. Additionally, the third and fourth segments 35 and 36 are respectively divided into two smaller segments 35a and 35b and two smaller segments 36a and 36b by a fourth partition 37 orthogonal to the third partition 32. The respective partitions 30, 31, 32 and 37 are formed by partially welding the two films constituting the back pad 26, and a communication hole 38 is formed between the respective adjacent segments.

Air supplied from the pump 29 through the air inlet 27 is sequentially supplied to the first segment 33, the second segment 34, the smaller segments 35a and 35b of the third segment 35, and the smaller segments 36a and 36b of the fourth segment 36, and expands each of these segments. However, since the tip 39 of the back pad 26 is closed, it is not inflated with air. The tip 39 of the back pad 26 includes a hole 39a for suspension. As to capacities of the respective segments, the second segment 34 has the largest capacity. The capacities of the first segment 33, the third segment 35 and the fourth segment 36 are substantially equal to each other, but they are set smaller than that of the second segment 34. Further, the capacities of the respective smaller segments 35a, 35b, 36a and 36b are set to be substantially equal to each other.

When the user wears the vest 11 accommodating the back pad 26 inflated with air, the back pad 26 is arranged along the backbone of the user. The tip 39 of the pad 26 is arranged at the base of the neck, the fourth segment 36 and the third segment 35 are arranged in the vicinity of the blade bones, and the second segment 34 and the first segment 33 are arranged in the vicinity of the back side of the lower abdominal region.

Figure 5:
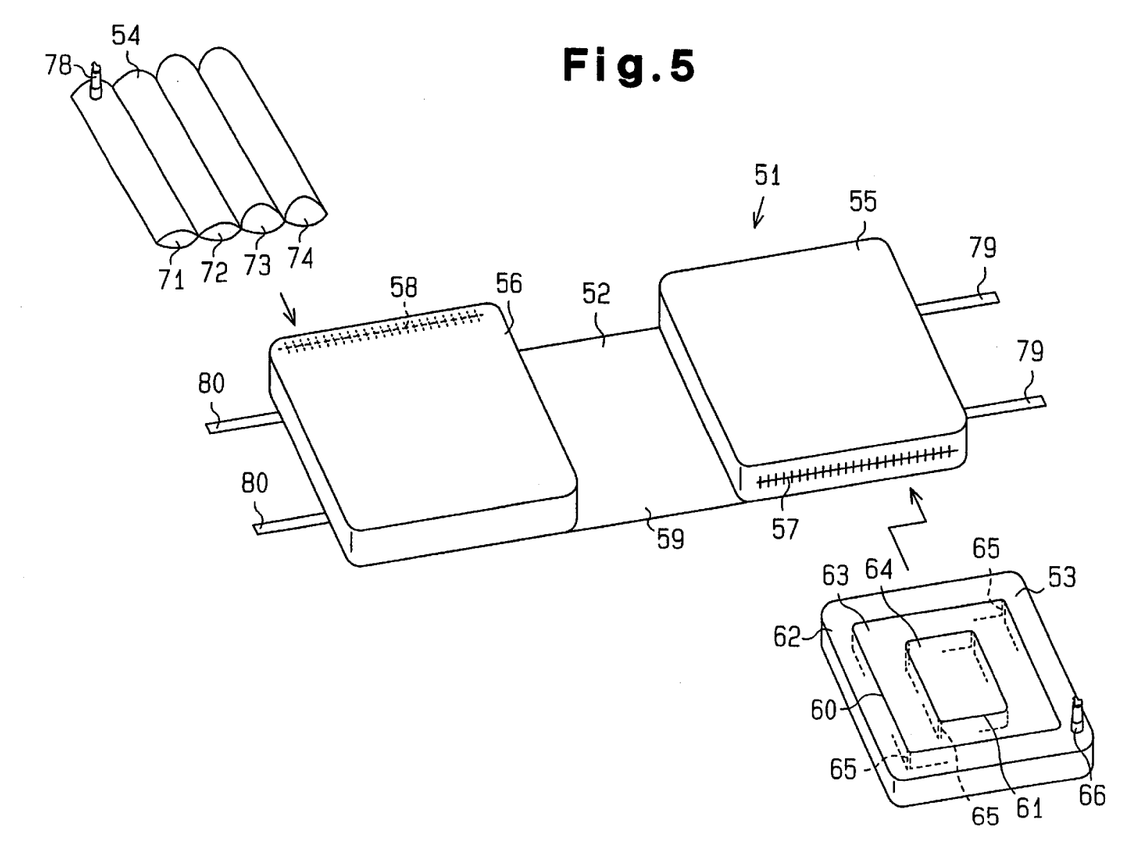
FIG. 5 is an exploded perspective view of a pillow used in combination with the vest illustrated in FIG. 1.

Description will now be given as to a pillow 51 which can be used together with the vest 11. As shown in FIG. 5, the pillow 51 is constituted by pouch 52 and two pads 53 and 54. The pouch 52 is formed of a cotton cloth and has two accommodation portions 55 and 56. First and second accommodation portions 55 and 56 are respectively sewn so as to form each flattened cubic bag, and first and second fasteners 57 and 58 used for opening and closing an opening are attached to each one side of the first and second accommodation portions 55 and 56. The first and second fasteners 57 and 58 are attached on the opposed side surfaces of the first and second accommodation portions 55 and 56. The first and second accommodation portions 55 and 56 are connected by a connection piece 59.

A first pad 53 is removably accommodated in the first accommodation portion 55, and a second pad 54 is removably accommodated in the second accommodation portion 56. The first pad 53 is formed into a flattened cubic shape by a synthetic resin film. The inside of the first pad 53 is partitioned by two partition walls 60 and 61 having the plane rectangular shape, thereby forming three segments 62, 63 and 64. Slits 65 are formed at corners of the respective partition walls 60 and 61, and the respective segments 62, 63 and 64 can communicate with each other through these slits 65. An air injection valve 66 formed of an elastic material is attached to the outer segment 62. Therefore, by injecting air into the outer segment 62 of the first pad 53 through the air injection valve 66, the air is supplied to each segment through each slit 65, and each segment can thereby be expanded in the order of the inner segment 64, the middle segment 63 and the outer segment 62. The first pad 53 expanded with air is accommodated in the first accommodation portion 55.

The second pad 54 is formed by two synthetic resin films, and has four segments communicating with each other, i.e., first to fourth segments 71 to 74. Each of the segments 71 to 74 is formed into the sheath shape, and the respective segments are partitioned by welding the two films at the boundary between the respective segments.

An air injection valve 78 similar to the air injection valve 66 of the first pad 53 is connected to the first segment 71. Therefore, by injecting air into the first segment 71 through the air injection valve 78, the air is supplied to each segment through the communication hole (not shown) between the respective segments, thereby sequentially expanding the fourth segment 74 to the first segment 71. The second pad 54 expanded with air is accommodated in the second accommodation portion 56. The capacity of each of the third and fourth segments 73 and 74 is set to substantially double the capacity of each of the first and second segments 71 and 72, and the height of each of the third and fourth segments having air filled therein is substantially double the height of each of the first and second segments 71 and 72.

Strings 79 and 80 are attached to the first accommodation portion 55 and the second accommodation portion 56, and the both accommodation portions 55 and 56 are fixed by interknotting the strings 79 and 80 each other with the both accommodation portions 55 and 56 overlapping each other.

Description will now be given on the procedure of using the vest 11 and the pillow 51 having the above-described structure. At first, when preparing the vest 11, air is injected into the back pad 26 by manipulating the pump 29 shown in FIGS. 2(a) and 2(b) so that the back pad 26 is expanded. At this moment, the air is supplied to the respective segments 33, 34, 35 and 36 through the communication hole 38.

Then, the opening of the accommodation portion 24 is opened by the fastener 25, the back pad 26 is inserted into the accommodation portion 24 through the opening, and the entire back pad 26 is arranged in the accommodation portion 24. Subsequently, with a part of the tube 28 and the pump 29 being suspended to the outside from the opening of the accommodation portion 24, the opening of the accommodation portion 24 is closed by the fastener 25. Thereafter, the position of the back pad 26 is finely adjusted according to needs. At this point in time, preparation of the vest 11 is completed.

Figure 3:
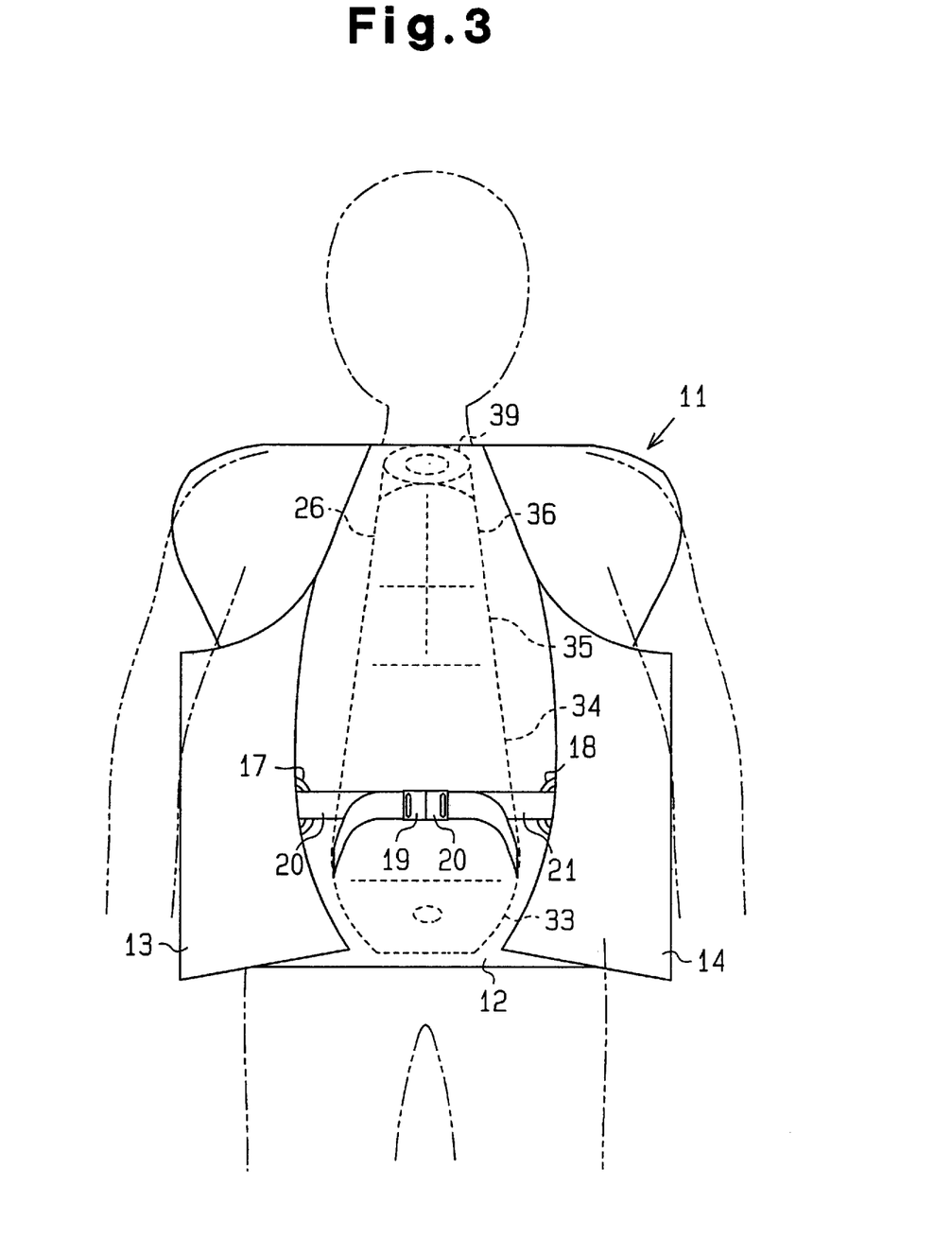
FIG. 3 is a front view showing a wearing of the vest illustrated in FIG. 1.

When wearing the vest 11, the user inserts the arms into the right hole 15 and the left hole 16 of the vest 16, and the tongue 19 is then engaged with the buckle 19a as shown in FIG. 3, thereby securely fixing the vest 11 to the body of the user. In this state, by fixing the respective clamps 22 and 23 to each other, the right front body 13 is fixed to the left front body 14.

Figure 4:
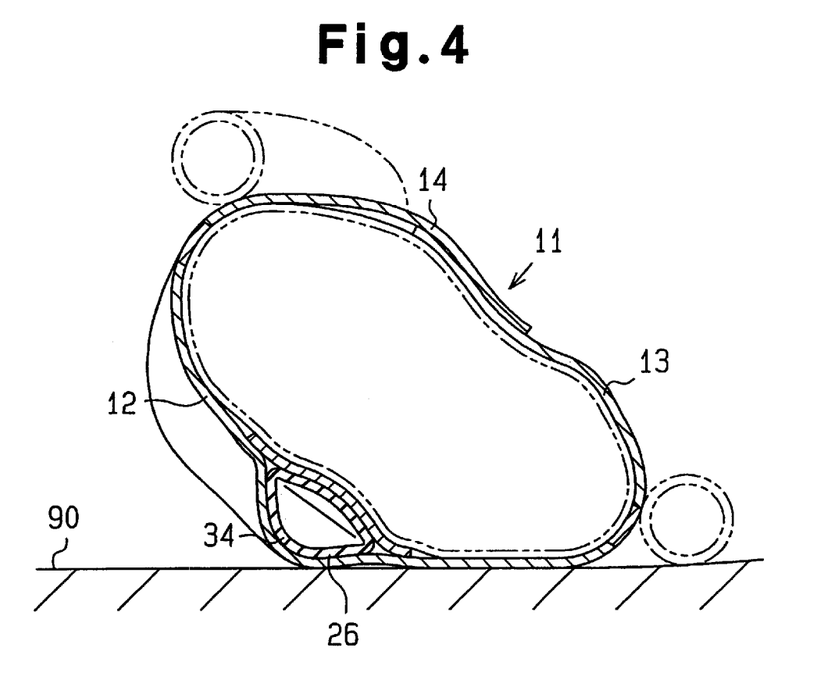
FIG. 4 is an explanatory view showing a recumbent state of a user wearing the vest depicted in FIG. 1.

When the user is wearing the vest 11, the back pad 26 is arranged along the backbone of the user. The tip 39 of the back pad 26 is arranged at the base of the neck of the user, the fourth segment 36 and the third segment 35 are arranged in the vicinity of the blade bones, and the second segment 34 and the first segment 33 are arranged in the vicinity of the back side of the lower abdominal region. Therefore, as shown in FIG. 4, the expanded back pad 26 is pressed against the body of the user so as to be parallel with the backbone, and the central part of the back of the body protrudes along the backbone. The degree of expansion is sequentially increased from the base of the neck toward the lower abdominal region of the user, and then decreased in accordance with the capacity of each segment.

Therefore, when the user wearing the vest 11 is lying face up on a bed 90, the central part of the back of the body is supported by the back pad 26, and the posture in which the left shoulder or the right shoulder is spaced from the bed, namely the posture in which the upper half of the body is inclined at a predetermined angle is maintained. At this moment, the head is inclined so as to form a predetermined angle with respect to the bed so that the user can sleep in a comfortable posture. Therefore, it is possible to avoid the downward displacement of each organ such as the nose wings, the soft palate, the pendulous palate, the tongue root or the pharyngeal palate from the upper airway and prevent the user from lapsing into an apneic state during sleep.

Moreover, when the user tosses in his or her sleep, the air in the back pad 26 moderately moves by turning the upper half of the body the other way so as to separate from the bed 90 one shoulder which is in contact with the bed 90. Therefore, the user can easily toss as substantially similar to the case when not wearing the vest 11. At this moment, since the expanded part of the back pad 26 does not exist around the base of the neck and the expansion of the back pad 26 around the blade bones is set small, the back pad 26 will not interfere with the user in tossing in his or her sleep.

On the other hand, when preparing the pillow 51, air is injected into the first pad 53 through the air injection valve 66 of the first pad 53 in order to inflate the first pad 53. At this moment, the air is supplied to the respective segments 62, 63 and 64 through the slits 65.

Then, the opening of the first accommodation portion 55 is opened by the fastener 57, and the first pad 53 is inserted into the first accommodation portion 55 through the opening. Thereafter, the opening of the first accommodation portion 55 is closed by the fastener 57.

Subsequently, air is injected into the second pad 54 through the air injection valve 78 of the second pad 54 in order to inflate the second pad 54. At this moment, the air is supplied to the respective segments 71 to 74 through the communication holes (not shown) between the respective segments 71 to 74.

Figure 6:
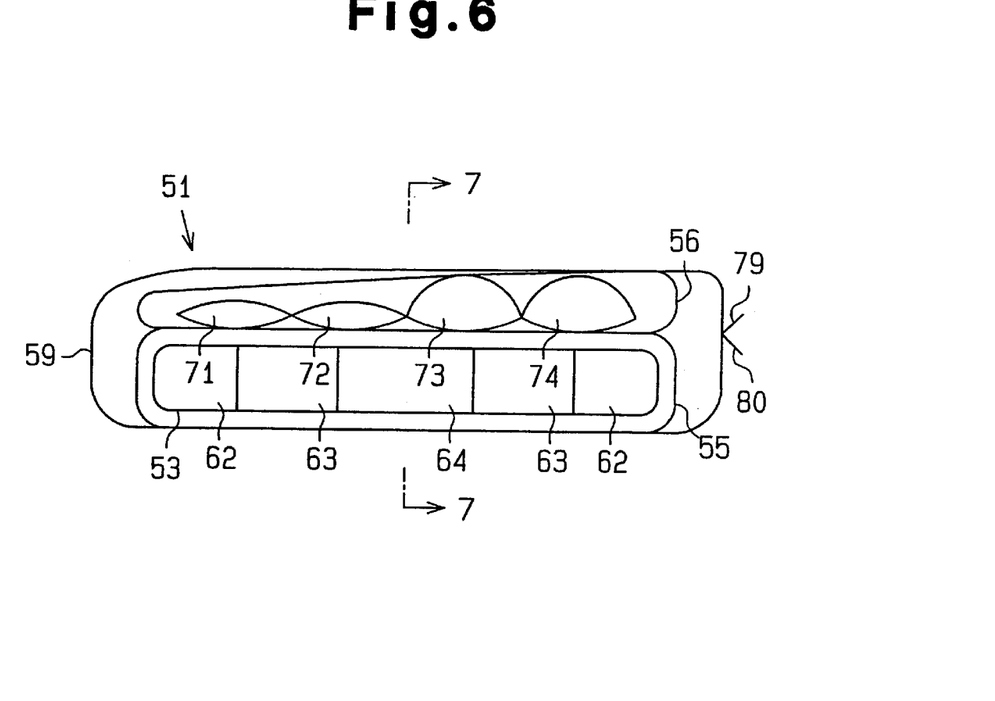
FIG. 6 is a cross-sectional view showing the pillow depicted in FIG. 5.

Then, the opening of the second accommodation portion 56 is opened by the fastener 58, and the second pad 54 is inserted therethrough into the second accommodation portion 56. Thereafter, the opening of the second accommodation portion 56 is closed by the fastener 58. Finally, the first and second accommodation portions 55 and 56 are overlapped as shown in FIG. 6, the second accommodation portion 56 being arranged on the first accommodation portion 55, and the strings 79 and 80 are interknotted, thereby completing the pillow 51.

Figure 7:
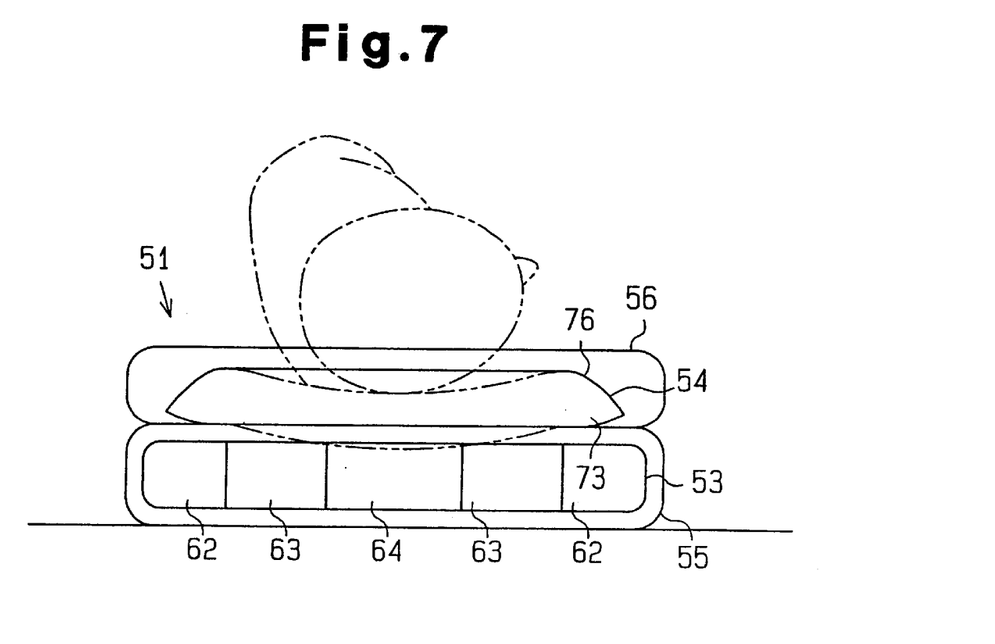
FIG. 7 is a cross-sectional view of the pillow taken along line 7—7 in FIG. 6.

As shown in FIG. 7, by placing the head of the user on the pillow 51 in such a manner that the head crosses the lengthwise direction of the respective segments 71 to 74 of the first pad 53, the first pad 53 deforms by the weight of the head from a position indicated by a solid line to a position indicated by a two-dot chain line in FIG. 7. That is because the air in the respective segments 71 to 74 is moved from the central part of each of the segments 71 to 74 toward the both ends due to the weight of the head.

In this state, the weight of the head is also applied to the second pad 54 through the first pad 53 so that the second pad 54 also deforms as similar the to the first pad 53 although not shown. That is because the air in the central segment 64 of the second pad 54 is moved to the middle segment 63 and the outer segment 62 through the slits 65 due to the weight of the head.

Therefore, as shown in FIG. 7, by placing the head of the user on the pillow 51 when the user wearing the above-described vest 11 lies on his or her side, the head can securely be inclined as similar to the upper half of the body, and this state can stably be maintained for a long period of time. It is to be noted that the hardness of the pillow 51 can be adjusted in accordance with preferences of the user by appropriately increasing or decreasing the quantity of the air to be supplied to the first pad 53 and the second pad 54.

As described above, according to the present invention, the following advantages can be obtained.

In this embodiment, the pad 26 which extends in the longitudinal direction is provided to the back body 12 of the vest 11. In addition, a plurality of the segments 33 to 36 arranged along the longitudinal direction are provided in the pad 26, and the segments 33 to 36 have different capacities. The respective segments 33 to 36 are inflated in accordance with the capacities thereof by using the air supplied to the respective segments 33 to 36. Therefore, the user wearing the vest 11 can maintain his or her body inclined for a long period of time while asleep, and hence it is possible to prevent the user from lapsing into an apneic state during sleep.

Additionally, when the user wears the vest 11 accommodating therein the pad 26 expanded with air, the pad 26 is arranged along the backbone of the user. At this moment, the flat end of the pad 26 is arranged at the base of the neck, and the fourth segment 36 and the third segment 35 with smaller expansion are arranged in the vicinity of the blade bones. Therefore, the back pad 26 will not interfere with the user in tossing in his or her sleep. Since the pillow 51 can be used together with the vest 11, the head can securely be inclined as similar to the upper half of the body, thereby stably maintaining that state for a long period of time.

Further, the pillow 51 is constituted by the case body 52 formed of a cloth, the first pad 53 accommodated in the first accommodation portion 55 of the case body 52, and the second pad 54 accommodated in the second accommodation portion 56 of the case body 52, and the first accommodation portion 55 and the second accommodation portion 56 are connected to each other with the first pad 53 and the second pad 54 overlapping each other. Therefore, the pillow 51 can be simplified in structure and inexpensive in manufacture.

Incidentally, the present invention is not restricted to the above-described embodiment, and a gas other than air or a liquid such as water may be used as a fluid supplied to the respective pads 26, 53 and 54, for example. Moreover, the respective pads 26, 53 and 54 may be formed of synthetic rubber.

What is claimed is:

1. A gear for preventing a user from lapsing into an apneic state by maintaining the body of said user to an inclined posture during said user's sleep, said gear comprising:

a clothing body worn by said user, said clothing body including a back body and a front body; and a pad which is attached to said back body of said clothing body and extends in the longitudinal direction, wherein said pad includes a plurality of segments arranged along the longitudinal direction, wherein capacities of said segments is different from each other, and wherein each of said segments is inflated in accordance with its capacity by a fluid supplied to each of said segments, wherein a bag-shaped accommodation portion is formed in said back body of said clothing body, and wherein said pad is removably accommodated in said accommodation portion.

2. The gear according to claim 1, wherein said clothing body is a vest.

3. The gear according to claim 1, wherein said pad is formed into a hollow bag shape by welding peripheral edges of two synthetic resin films and includes an injection opening for a fluid.

4. The gear according to claim 3, wherein the inside of said pad is partitioned into first, second, third and fourth segments by first, second and third partitions extending in the widthwise direction of said pad, wherein each of said third and fourth segments is divided into two small segments by a fourth partition orthogonal to said third partition, wherein each partition is formed by partially welding two films constituting said pad, and wherein a communication hole is formed between said respective adjacent segments.

5. The gear according to claim 4, wherein capacities of said first segment, said third segment and said fourth segment are set substantially equal to each other and smaller than the capacity of said second segment.

6. The gear according to claim 4, wherein capacities of said respective smaller segments are set substantially equal to each other.

7. The gear according to claim 4, wherein, when said user wears said vest accommodating therein said pad expanded with a fluid, said pad is arranged along the backbone of said user, wherein the tip of said pad is arranged at the base of the neck, wherein said fourth segment and said third segment are arranged in the vicinity of the blade bones, and wherein said second segment is arranged in the vicinity of the back side of the lower abdominal region.

8. The gear according to claim 1, wherein said fluid is air.

9. The gear according to claim 1, further comprising a pillow used in combination with said clothing body, wherein said pillow comprises:

a pouch formed of a cloth, said pouch having a first accommodation portion and a second accommodation portion;

a first pad accommodated in said first accommodation portions; and a second pad accommodated in said second accommodation portion, wherein said first accommodation portion and said second accommodation portion being connected to each other with said first pad and said second pad overlapping each other.

10. The gear according to claim 9, wherein said first pad is formed into a flattened cubic shape by using a synthetic resin film, wherein the inside of said first pad is partitioned by two partition walls so that three segments are formed, wherein a slit is formed in each of said partition walls, wherein said respective segments communicate to each other through said slits, and wherein a fluid is supplied to said respective segments through said slits by injecting said fluid to one of said segments, thereby expanding said respective segments.

11. The gear according to claim 9, wherein said second pad is formed by two synthetic resin films and has four segments communicating with each other, wherein said respective segments are partitioned so as to communicate with each other by welding the two films at the boundary between said respective segments, and wherein said respective segments are sequentially expanded by injecting a fluid to one of said segments.

12. The gear according to claim 11, wherein each of said segments of said second pad is formed into a sheath shape.

* * * * *